United States Patent [19]

Lainio et al.

[11] Patent Number: 5,698,789
[45] Date of Patent: Dec. 16, 1997

[54] METHOD AND DEVICE FOR MEASURING THE PROPERTIES OF GRANULAR EARTH MATERIALS

[75] Inventors: Kai Juhani Lainio, Turenki; Ilmari Paakkinen, Moinsalmentie 1854, FIN-57230 Savonlinna, both of Finland

[73] Assignee: Ilmari Paakkinen, Savonlinna, Finland

[21] Appl. No.: 633,725

[22] PCT Filed: Oct. 25, 1994

[86] PCT No.: PCT/FI94/00480

§ 371 Date: Apr. 22, 1996

§ 102(e) Date: Apr. 22, 1996

[87] PCT Pub. No.: WO95/12116

PCT Pub. Date: May 4, 1995

[30] Foreign Application Priority Data

Oct. 26, 1993 [FI] Finland .................. 934730

[51] Int. Cl.$^6$ ........................................ G01N 3/08
[52] U.S. Cl. ........................................ 73/824; 73/843
[58] Field of Search .................. 73/805, 813, 814, 73/822, 824, 843, 858, 854, 54.01, 54.37, 54.39

[56] References Cited

U.S. PATENT DOCUMENTS

| | | |
|---|---|---|
| 3,461,717 | 8/1969 | Dunlap et al. . |
| 3,465,575 | 9/1969 | Kepes . |
| 4,095,461 | 6/1978 | Starita . |
| 4,794,799 | 1/1989 | Paakkinen . |
| 4,930,346 | 6/1990 | Paakkinen et al. . |
| 5,103,679 | 4/1992 | Porter et al. .............. 73/843 |
| 5,481,903 | 1/1996 | King et al. .............. 73/54.28 |

FOREIGN PATENT DOCUMENTS

94/00480 10/1994 WIPO .

OTHER PUBLICATIONS

S.F. Brown "Lecture I: Bituminous Materials: Elastic Stiffness and Permanent Deformation", I.1–I.11.

Primary Examiner—Richard Chilcot
Assistant Examiner—Max H. Noori
Attorney, Agent, or Firm—Scully, Scott, Murphy & Presser

[57] ABSTRACT

The invention relates to a method and device for measuring the properties of earth materials subjected to a load, the device comprising a cylinder (10) for a material sample enclosed by a cover and bottom plate (6a, 7a), compressing the sample, and making the central axes of the cover and bottom plate deviate parallel to each other by an angle in relation to the central axis of the cylinder and in the same plane with the central axis of the cylinder. The central axes of the cover and bottom plate revolve about the central axis of the cylinder (10) with an angular deviation so as to deform the sample. In order to make the measuring more effective the material is measured by means of a device which is provided for measuring the force resisting the deformation of the sample in the direction of the radius of the sample, and for measuring the force resisting the deformation of the sample in the direction of rotation of the angular deviation.

7 Claims, 2 Drawing Sheets

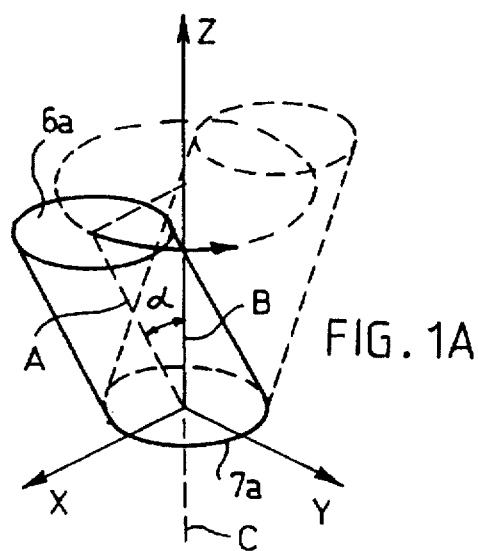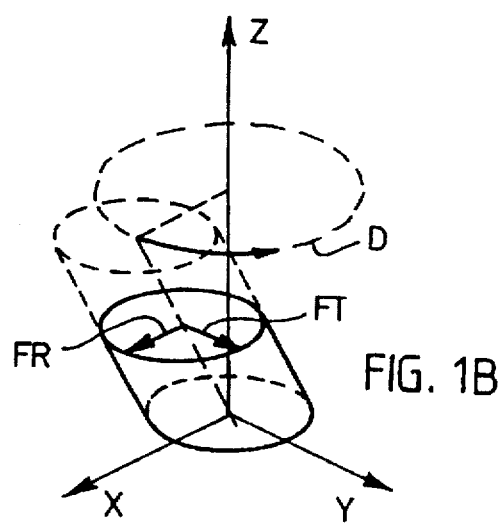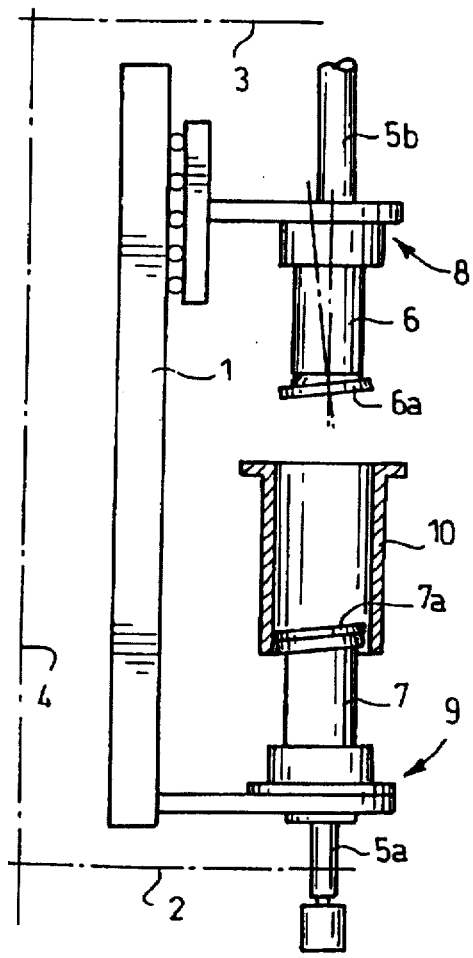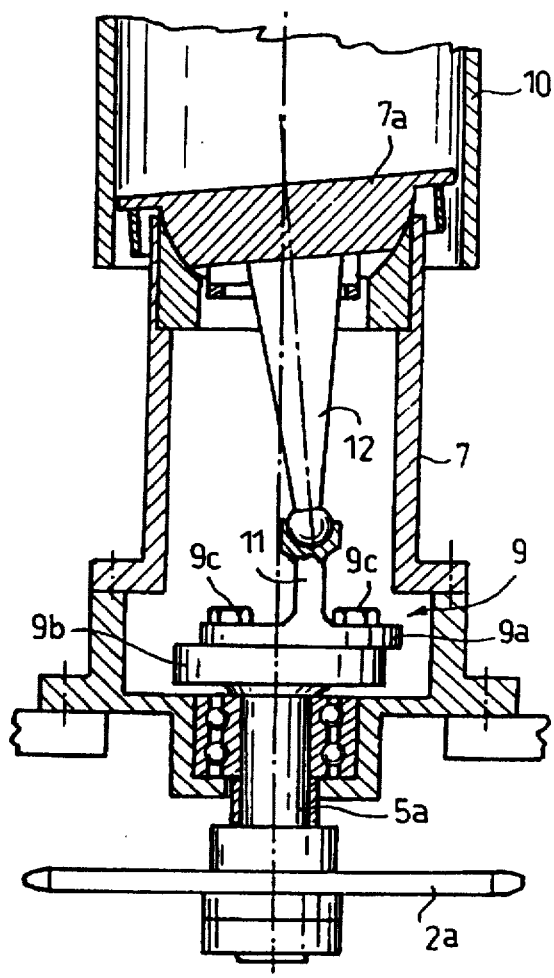

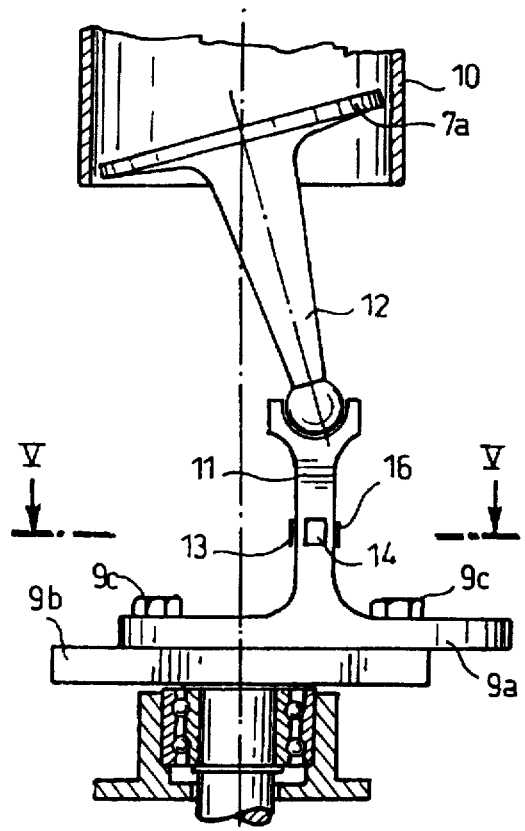
FIG. 4
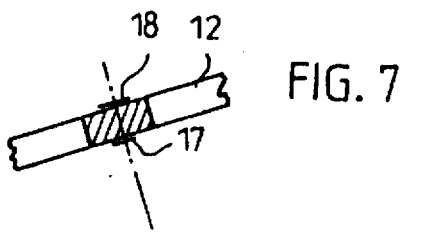
FIG. 7
FIG. 6
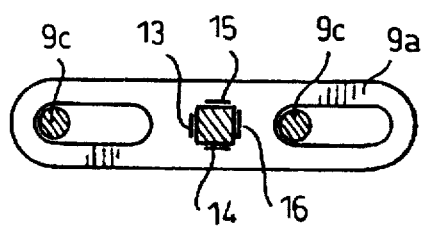
FIG. 5

METHOD AND DEVICE FOR MEASURING THE PROPERTIES OF GRANULAR EARTH MATERIALS

The invention relates to a method for measuring the properties, such as elastic, plastic and viscous deformation resistances, of granular earth materials subjected to a load, according to which method

- a sample taken from a material is compressed with a constant force in a cylinder between a planar bottom plate and cover plate of the cylinder,
- the central axes perpendicular to the bottom and cover plate are made to deviate by an angle from the central axis of the cylinder in the same plane and in the same direction,
- the sample is deformed under a constant compression between said plates by changing the position of the plates rotationally in relation to the central axis of the cylinder with the plates remaining parallel to each other, and
- deformations and corresponding stresses in the sample are measured.

In this connection, earth materials refer to gravel, sand, crushed aggregates including crushed rock, stiff fresh concrete and other similar granular components.

Information is needed in earthwork about the suitability of the earth material for each particular purpose, for example about the changing of earth materials under traffic loads in road construction, the behaviour of the foundations of buildings in earthquake areas, the bearing capacity of the sea bottom under a leg of a drilling rig, and the behaviour of a granular material during transportation and compaction.

Elastic, or reversible, deformations occur in earth materials subjected to a load. If the load is heavy enough, it also causes plastic, or irreversible, deformations in the earth material, and these often lead to the damaging of the structure.

If the material comprises stiff viscous components, it behaves in a viscoelastoplastic way, in which case a viscous deformation resistance appears in the same way as a plastic resistance. This phenomenon is well known from materials, such as asphalt, which are used for road pavement and have some bitumen mixed in them. A special feature of a viscous resistance is that it decreases if the sliding speed is reduced or the temperature of the sample is increased. By means of these measures, a viscous and plastic resistance can be distinguished from each other.

When the foundation of a device or a building is designed to carry periodic loads, the aim is that there will be no detrimental, irreversible (plastic) deformations in the ground soil. Therefore it is important that both the elastic and plastic behaviour of the material can be measured as reliably as possible especially in the borderland between these two phenomena. The strengths of a material and the facts about its behaviour measured by prior methods have been approximate, since measuring has been difficult and inexact.

Transfers of large earth materials are preferably avoided during building due to costs. Therefore, information is desired about the properties of all usable materials situated near the building site. Different materials, for example gravel and crushed aggregate, are often mixed in construction. Then the properties of the mixed material have to be controlled by continuous measurements. In these measurements it is also important that the elastic and plastic behaviour of the material can be measured separately.

It is also important to know the viscous properties of the material in developing and testing asphalt and in paving roads, so that the compaction properties of the aggregate, the amount of bitumen, and the viscosity could be proportioned to each other in making the asphalt material.

The elastic and plastic deformations and stresses of an earth material under periodic loads are generally measured in laboratories by means of for example a shear box and a so-called triaxial tester. There are several practical problems in these tests. The movement in the tests takes place back and forth in one direction. To achieve such a periodic movement, complex and expensive equipment is required. The study of great deformations, i.e. the plastic area, is not particularly exact, since the field of deformation of the sample in each device is very non-homogenous. Due to these and also to other reasons, there is a great deal of deviation in the results, and therefore they are not very reliable.

A method and an apparatus for measuring the properties of a stiff, granular material, in particular its compactibility, are previously known from Finnish Patent 75,672. According to this method, a sample of a known weight is taken from the material, the sample is compressed with a constant force from two opposite directions and shear-compacted under a constant compression between two parallel inclined planes which change position by revolving, for exerting a shear compaction effect on the sample. The volume of the sample is measured in the beginning of the compaction and after a predetermined compaction, and the change in the volume of the sample is compared to experimentally determined limit values.

The magnitude of the torque resisting the revolving of the inclined planes is measured from the sample by said known method, so that information is obtained about the plastic deformations and stresses of different materials. The elastic stresses caused by the elastic deformations of the earth materials are in turn measured by the above described laboratory equipment.

The purpose of this invention is to provide a method which makes it possible to measure the elastic, plastic and also viscous properties of a material in a reliable way. This is achieved by the method according to the invention, which is characterized in that forces resisting the deformations in the sample are measured from the sample both in the direction of the angular deviation (the radius of the sample) to determine the elastic deformation resistance, and in the direction of rotation of the angular deviation to determine the plastic and possible viscous deformation resistance.

By the method according to the invention, the elastic and plastic behaviour of a material can be monitored as separate events during the same round of measurement. Due to this, the elastic and plastic stresses of the material are measured in a situation equivalent to real conditions, since in practice the material is simultaneously under loads causing both elastic and plastic deformations.

When the deformation of the material is elastic, the stresses are also elastic. When the deformation is greater and in part plastic, the material comprises both kinds of stresses. When the load is removed, the reversible deformations remain but both stresses disappear. Plastic stress is the "resistance" of the irreversible deformation. When a mathematical model is constructed for example for the behaviour of the structural layers of a road, information is needed simultaneously, in the same density, about the elastic stresses as well as about the deformation and the plastic deformation resistance. To provide continuous, complete information about the stresses and deformation for this purpose, it is preferable to measure them simultaneously. It has been very difficult to obtain separate, reliable, individual measurement results by present methods, since it has been necessary to conduct several tests by different devices. While the samples are prepared, errors remain in their densities, and the results have been unreliable.

When both the elastic and plastic behaviour of the materials are known, it is possible to compare the bearing capacity and operating characteristics of the materials and to select materials suitable for example for road construction.

The invention also relates to a device for carrying out the above described method in practice, and this device is characterized by what is disclosed in claim 5.

By means of the device according to the invention, the method according to the invention can be realized and the advantages provided by the method can be achieved by means of simple devices.

The invention will be described in the following in greater detail with reference to the accompanying drawings, in which FIGS. 1A and 1B represent schematically the operating principle of the method according to the invention, FIG. 2 is a front view of the structure of a device to be used in the method according to the invention, in a filling position, FIG. 3 shows one detail of the device of FIG. 2 on a larger scale, FIGS. 4 and 5 show a first embodiment of the device according to the invention, and FIGS. 6 and 7 show a second embodiment of the device according to the invention.

The material sample 1 shown in FIG. 1A of the drawings is cylindrical and is enclosed between a bottom 7a and a cover 6a. The bottom and the cover are mutually parallel, but the centre line A of the cylinder deviates by an angle $\alpha$ from the direction of the normal B of the bottom and the cover. This deviation $\alpha$ is the angle of movement of the cylinder.

The sample is rotated about the axis of rotation C which coincides with the normal B of the bottom with the angle of movement remaining unchanged, whereby the angle of movement travels evenly about the axis of rotation C of the sample. The bottom and the cover remain parallel and do not revolve about their centre (the normal B), but move with the angle of movement.

FIG. 1B shows a cross-section of the material sample. When the sample is rotated about the axis of rotation with said angle of movement, shear forces are generated in the material. The resultant FR of the shear forces in the cross-sectional surface is parallel to the angle $\alpha$, i.e. the radius of the sample, and rotates with this angle.

If the deformation is completely elastic, the angle of movement and the resultant FR drop back to zero, when the material sample is no longer rotated and the sample is released.

When the material sample is rotated with a larger angle of movement in relation to the axis of rotation C, both the resultant FR of the elastic shear forces and the resultant FT of the plastic shear forces act on the cross-sectional surface of the material. The elastic resultant FR resists the elastic deformation, i.e. the change in the angle of movement. The plastic resultant FT resists the plastic deformation, i.e. the rotation of the angle of movement. The direction of the plastic resultant is parallel to the tangent of the path D of the angle of movement, as shown in FIG. 1B. These two forces, i.e. the stresses occurring in the sample, can be distinguished from each other on the basis of their direction of action.

The compressive force under which the sample is maintained during the measuring is of the same magnitude as the force with which the material will be loaded in its place of use. For example in road construction, the highest pressure under a wheel of a lorry is about 0.6 to 1 MPa.

The rotation speed has to be so low that the accelerating forces do not interfere with the measurement. The highest speeds are for example 80 to 150 rpm. When asphalt is being studied, the viscosity of the bitumen makes the material stiff, and therefore a suitable speed is 10 to 30 rpm.

The angle of movement is usually 1° to 3° when a compaction of the material is desired. When only the elastic area is studied, a smaller angle of movement can be selected, for example 0.2° to 0.5°.

The elastic force resultant FR and the plastic force resultant FT can be measured by means of equipment similar to that disclosed in Finnish Patent 75,672, but suitably modified. In the apparatus according to the Finnish Patent, the material sample does not revolve during the measuring, and neither does the round bottom plate or the cover plate. Only the upper piston and the lower piston which have bevelled heads by which the pistons press against the bottom and cover plate revolve about an axis of rotation coinciding with the central axis of the sample.

FIG. 2 shows in principle the device of Finnish Patent 75,672 modified so that it can be used in applying the method according to the invention. A frame of the device is denoted in principle in FIG. 2 by reference numeral 1. Transmission means, for example chains or cogged belts, are denoted in turn in FIG. 2 by reference numerals 2 and 3, and an intermediate shaft is denoted by reference numeral 4. By means of these elements, the rotating motions of axes of rotation 5b, 5a of an upper and lower piston 6, 7 are synchronized. Eccentric devices 8, 9 are placed in connection with the rotating mechanisms of the upper and lower piston 6, 7 of the measuring equipment, and by means of the eccentric devices the central axes of the pistons can be made to deviate by an angle of movement in relation to the axis of rotation C coinciding with the central axis of the sample. The eccentric devices of the upper and lower piston are rotated synchronously as stated above, whereby the bottom 7a and the cover 6a revolve with the angle of movement about the axis of rotation without revolving about their central axes. Thus the bottom and the cover are forced to perform a revolving undulating motion against the end surfaces of the material sample. A working cylinder where the material sample to be measured is placed is denoted by reference numeral 10.

The axis of rotation 5b is preferably an axis extendable in its longitudinal direction, in which case the upper piston 6 can be slideably mounted on the frame 1 by means of bearings so that the material in the cylinder 10 can be compressed in the axial direction of the cylinder 10. The aforementioned compressive motion can be achieved by means of any device known per se. At the lower end of the axis of rotation 5a there is also a collector by means of which electric signals can be obtained from the device.

FIG. 3 shows the rotating mechanism of the lower piston on a larger scale. The same reference numerals are used for corresponding parts in FIG. 3 as in FIG. 2. In addition, a chain wheel arranged to operate together with the transmission device 2 is denoted in FIG. 3 by reference numeral 2a. The eccentric structure is formed by two planar elements 9a and 9b. The position of the planar elements 9a, 9b with respect to each other can be adjusted by means of screws 9c. The bottom 7a is attached to a rod part 11 of element 9a by means of a pivot arm 12.

The moving mechanism of the cover 6a is mechanically completely equivalent to the above described moving mechanism of the bottom 7a. The only difference is the measuring arrangement which is found only in connection with the moving mechanism of the bottom. The starting point of the invention is that equal forces prevail in the bottom and the cover. The measuring arrangement will be described in greater detail further on.

For measuring the aforementioned forces FR and FT, measuring sensors are placed in the moving mechanism of the bottom. For example strain gages, generally used in scales and in measuring forces, can be used as such sensors, the strain gages being attached to the mechanical parts of the machine to measure tensile and compressive stresses. The forces to be measured produce bending stresses in the components of the machine. The measuring sensors are positioned in such a way that they detect such stresses as clearly as possible. FIGS. 4 to 7 show two examples of practical measuring arrangements.

In the embodiment of FIGS. 4 and 5, strain gages 13 to 16 are placed in the rotating rod part 11 of the eccentric device. The strain gages 13 and 16 are placed in the rod part 11 having a square cross-section in such a way that a force FR parallel to the radius of the eccentric motion produces in the strain gages a clear change of the electric current, i.e. a signal. Correspondingly, the strain gages 14 and 15 measure the forces FT parallel to the tangent. The positions of the strain gages are particularly apparent in FIG. 5.

FIGS. 6 and 7 show another embodiment. In this embodiment, only two strain gages 17 and 18 are used, and they are placed in the pivot arm 12. The positions of the strain gages 17, 18 are particularly apparent in FIG. 7. The strain gages 17 and 18 measure, in one direction, the bending moment acting on the pivot arm 12. The elastic and plastic stresses of the sample act on the bottom 7a. The direction of both stresses revolves with the eccentric axis of the device. An approach sensor 19 indicates the position of the eccentric device. The measurement signals can be obtained from the device by means of the aforementioned collector.

In the embodiment according to FIGS. 6 and 7, the measurement information supplied by the strain gages 17 and 18 indicates elastic forces FR when the direction of the angular deviation is the same as the direction of measurement of the gages. When the angular deviation is perpendicular to this direction, the measurement information indicates plastic forces FT.

As described above, it is essential to the invention that measuring sensors, such as strain gages, are attached to the eccentric structure of the device so as to measure forces FR and FT. There can be for example four or two measuring sensors arranged to measure forces parallel to the radius of the eccentric rod, and forces parallel to the tangent of the rotating movement of the eccentric rod. A force parallel to the radius thus indicates the elastic shear resistance occurring in the sample and resisting a deformation, and a force parallel to the tangent indicates the plastic and viscous stresses of the sample, which resist a deformation movement, i.e. the rotating movement.

Elastic and plastic stresses prevail in the sample. They depend on the magnitude of the deformation. The stress resists a deformation. When the sample is in a working cylinder, its stresses are reflected as forces or moments in the mechanical parts of the measuring equipment. It is difficult to measure the stresses inside the material, and therefore the forces or moments acting on the parts of the device are measured. When the force FS, which is parallel to the radius and which acts on the centre of the cover of the cylinder, and the moment (the force FT) parallel to the tangent are measured, stresses resisting an elastic and plastic deformation can be derived from these quantities.

The behaviour of the properties of concrete subjected to a load is described in *Fresh Concrete, Properties and Tests* (by Peter Bartos, Elsevier Science Publishers, Amsterdam, 1992). The theory of the plastic deformation of materials is described in *Theory of Perfectly Plastic Solids* (by J. Wiley & Sons, N.Y., 1951).

When there are viscous components in the sample, the behaviour of the sample in deformation is quite complex. By means of exact measurements, it is also possible to detect viscous slides in a granular material which in other respects behaves elastically. Also in this case, the viscous slides are characterized in that a rise in the temperature or a decrease in the sliding speed diminishes the stresses and simultaneously increases the viscous deformations.

The viscous stress is thus dependent on the sliding speed. It can be distinguished from the plastic stress of a granular material by varying the speed of the slide. Also, the viscous properties of a sample are almost always dependent on the temperature of the sample. A viscous stress (resistance) can also be distinguished from a plastic stress by monitoring the differences which appear in the behaviour of the sample when the temperature is varied.

The somewhat complex characteristics of a viscoelasto-plastic material are not discussed in greater detail in this connection. A normal asphalt material used as road pavement is an example of a material which can be studied according to this invention. These phenomena have been widely discussed in various publications, for example in *Time and temperature effects on the deformation of bitumen and bitumen-material mixtures* (by C. Van der Poel, Journ. Soc. Plastics Engs, 11, 1955), and in *Pavement Design, Elastic Stiffness* and *Permanent Deformation* (Lectures in Seminar "Bituminous Pavement", S. F. Brown, Oulu, September, 1993).

We claim:

1. A method for measuring properties comprising elastic, plastic and viscous deformation resistances, of granular soil materials subjected to a load, said method comprising:

a sample taken from one of the materials is compressed with a constant force in a cylinder between a planar bottom plate and a planar cover plate of the cylinder.

the central axes perpendicular to the bottom and cover plate are made to deviate by an angle from the central axis of the cylinder in the same plane and in the same direction while maintaining said central axes in alignment with each other, the sample is deformed under a constant compression between said plates by changing the position of the plates rotationally in relation to the central axis of the cylinder with the plates being continually maintained in a parallel relationship to each other, and measuring deformations and corresponding stresses in the sample by measuring forces resisting the deformation in the sample from the sample both in the direction of the angular deviation along the radius of the sample to determine the elastic deformation resistance, and in the direction of rotation of the angular deviation to determine any plastic and viscous deformation resistance.

2. A method according to claim 1, characterized in that a force acting in the direction of rotation is selectively measured at different rotational speeds and at different temperatures to distinguish the viscous deformation resistance from the plastic deformation resistance.

3. A method according to claim 1 or 2, characterized in that the central axes of the cylinder and its plates are rotated about the central axis of the bottom or cover plate, whereby the angular deviation between the central axis of the cylinder and the axes of the plates remains unchanged.

4. A method according to claim 1 or 2, characterized in that the central axes of the plates of the cylinder are rotated about the central axis of the cylinder, whereby the angular deviation between the central axis of the cylinder and the axes of the plates remains unchanged.

5. A device for measuring properties comprising elastic, plastic and viscous deformation resistances, of soil materials subjected to a load, the device comprising a cylinder (10) for a material sample enclosed between a cover and bottom plate (6a, 7a) which are constantly maintained in parallel with each other, means for compressing the sample, means for causing the central axes of the cover and bottom plate to deviate in parallel to each other by an angle in relation to the central axis of the cylinder and in the same plane with the central axis of the cylinder while maintaining the alignment between said central axes, means for rotating the central axes of the cover and bottom plate selectively about the central axis of the cylinder (10) with said angular deviation, or for causing the central axis of the cylinder to rotate about an axis of rotation parallel to the central axes of the cover and bottom plate (6a, 7a) so as to deform the sample, and means (13 to 16; 17, 18) for measuring the force (FR) resisting the deformation of the sample in the direction of the radius of the sample, and for measuring the force (FT) resisting the deformation of the sample in the direction of rotation of the angular deviation.

6. A device according to claim 5, characterized in that the means (13 to 16) comprise two sets of sensors (13, 16 and 15, 14), whereby one sensor set (13, 16) is arranged to measure the force (FR) parallel to the radius, and the other set (15, 14) to measure the force (FT) acting in the direction of rotation of the angular deviation.

7. A device according to claim 5, characterized in that it is provided with an instrument (19) for indicating the direction of the angular deviation between the central axes of the bottom and cover plate (7a, 6a), and the cylinder (10), and that the means (17, 18) comprise one sensor set which is arranged to measure forces (FR) parallel to the radius when the direction of the angular deviation is the same as the direction of measurement of the sensor set (17, 18), and to measure forces (FT) acting in the direction of rotation of the angular deviation when the angular deviation is perpendicular to the direction of measurement of the sensor set (17, 18).

* * * * *